(12) United States Patent
Lupton

(10) Patent No.: US 9,757,542 B2
(45) Date of Patent: Sep. 12, 2017

(54) CAPTURE DEVICE

(71) Applicant: Lake Region Manufacturing, Inc., Chaska, MN (US)

(72) Inventor: Henry W. Lupton, Oranmore (IE)

(73) Assignee: Lake Region Manufacturing, Inc., Chaska, MN (US)

( * ) Notice: Subject to any disclaimer, the term of this patent is extended or adjusted under 35 U.S.C. 154(b) by 816 days.

(21) Appl. No.: 13/895,663

(22) Filed: May 16, 2013

(65) Prior Publication Data

US 2013/0317485 A1 Nov. 28, 2013

Related U.S. Application Data

(60) Provisional application No. 61/648,322, filed on May 17, 2012.

(51) Int. Cl.
*A61M 25/09* (2006.01)
*A61B 17/22* (2006.01)
*A61B 17/221* (2006.01)

(52) U.S. Cl.
CPC .......... *A61M 25/09* (2013.01); *A61B 17/221* (2013.01); *A61M 25/09041* (2013.01); *A61B 2017/2215* (2013.01); *A61B 2017/22035* (2013.01)

(58) Field of Classification Search
CPC .......... A61M 25/09; A61M 25/09041; A61B 17/221; A61B 2017/22035; A61B 2017/2215
USPC .......................................................... 606/1
See application file for complete search history.

(56) References Cited

U.S. PATENT DOCUMENTS

| 5,290,247 | A | * | 3/1994 | Crittenden | ........ A61M 25/0169 604/171 |
|---|---|---|---|---|---|
| 5,693,066 | A | | 12/1997 | Golcoechea et al. | |
| 7,527,606 | B2 | | 5/2009 | Oepen | |
| 2005/0226402 | A1 | | 10/2005 | Hofmann | |
| 2007/0066975 | A1 | * | 3/2007 | Wong | ..................... A61B 18/24 606/45 |
| 2007/0185524 | A1 | | 8/2007 | Diaz et al. | |
| 2007/0250070 | A1 | | 10/2007 | Nobis et al. | |
| 2008/0009883 | A1 | | 1/2008 | Bieneman | |
| 2008/0221587 | A1 | | 9/2008 | Schwartz | |
| 2008/0306499 | A1 | | 12/2008 | Katoh et al. | |
| 2010/0004506 | A1 | * | 1/2010 | Saadat | ................ A61B 1/0008 600/109 |

FOREIGN PATENT DOCUMENTS

| WO | WO9717911 | 5/1997 |
|---|---|---|
| WO | WO9726936 | 7/1997 |
| WO | WO0020064 | 4/2000 |

OTHER PUBLICATIONS

International Search Report for PCT/US2013/041319 dated Aug. 12, 2013, 4 pages.
Extended EP Search—13790660.8 dtd Feb. 9, 2016.

* cited by examiner

*Primary Examiner* — Corrine McDermott
*Assistant Examiner* — Tin Nguyen
(74) *Attorney, Agent, or Firm* — Michael F. Scalise; Grady J. Frenchick

(57) ABSTRACT

The present invention relates to a device and a method for capturing a guidewire being progressed along the lumen of a bodily duct and to direct it into a catheter. In one aspect a catheter-based eccentric cone capture structure is used to engage and direct a guidewire oppositely approaching the capture structure.

18 Claims, 3 Drawing Sheets

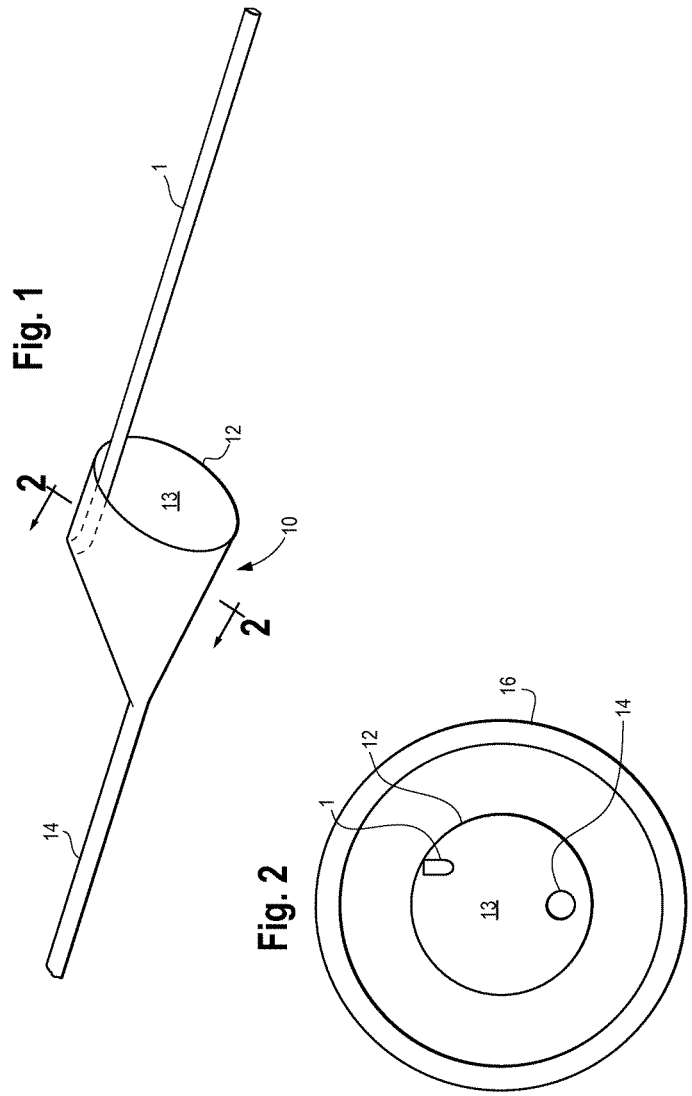

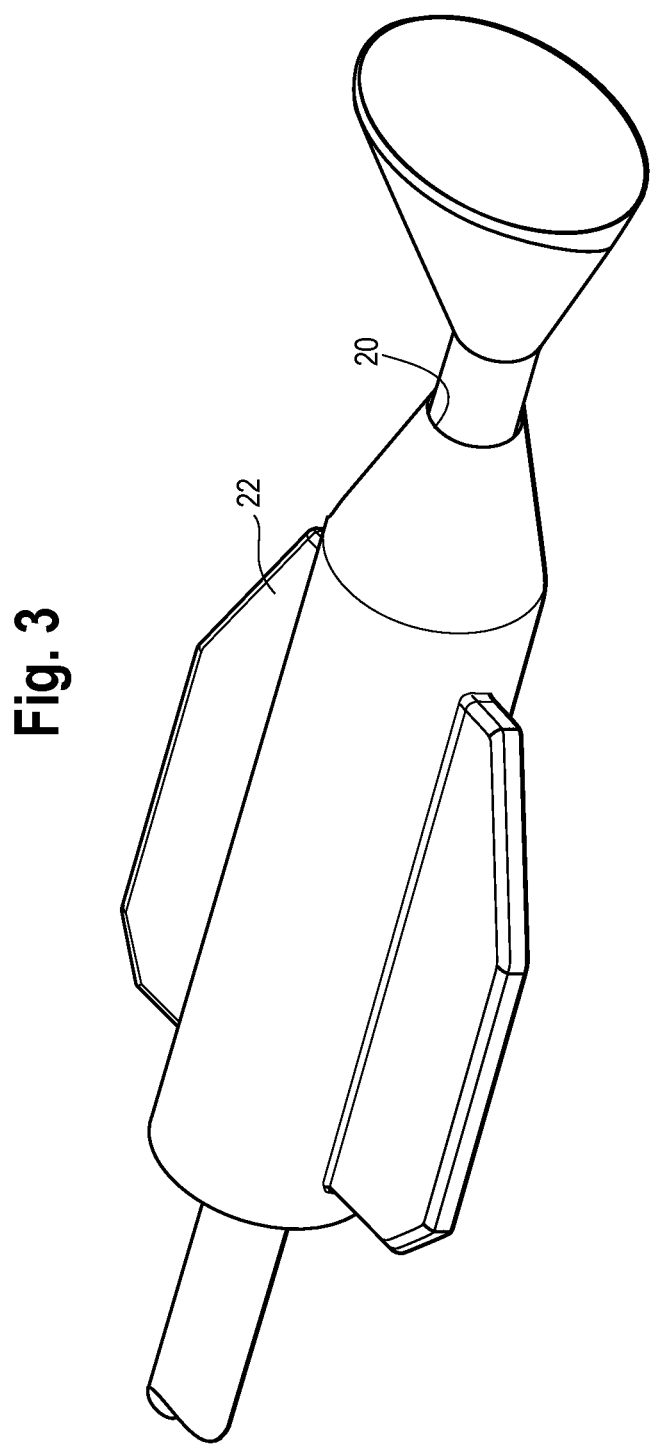

CAPTURE DEVICE

CROSS REFERENCE TO RELATED APPLICATIONS

This application is a nonprovisional of application Ser. No. 61/648,322 which was filed on May 17, 2012, the disclosure of which is incorporated by reference herein in its entirety.

FIELD OF THE INVENTION

The present invention relates to a device and a method for capturing a guidewire being progressed along the lumen of a bodily duct. More particularly the invention relates to such a device that is positioned at the end of a catheter and is adapted to be positioned within a bodily duct and is adapted to capture a guidewire being progressed through the bodily duct from the other direction and to direct it into the catheter.

The present invention relates to a new catheter or capture device that can be used to facilitate the capture of a guide and to a method of using such a catheter.

SUMMARY OF THE INVENTION

In the first aspect the present invention consists in a guidewire capture sheath for use in a bodily vessel comprising:
(a) a catheter having a longitudinal central axis and defining a lumen; and
(b) a capture means housed by, connected to, or integral with the catheter; at least a portion of the capture means being capable of expanding and collapsing between a first condition and at least a second condition, wherein when in the second condition, the capture means is adapted to guide a guidewire into the catheter, the capture means, comprising in its at least second condition is a distally-opening, eccentrically oriented cone, the cone being eccentrically oriented with respect to the longitudinal axis and being deployable from and retractable into the lumen.

In a preferred embodiment, when a portion of the capture means is in the first condition, it is contracted to a cross-sectional area that is smaller than that of the catheter; and when in the second condition, it is expanded to a cross-sectional area that is larger than that of the catheter.

In a second aspect, the present invention consists in a method for guiding a guidewire which is extending in a first vessel into a catheter, the method comprising:
(a) causing or allowing at least one portion of a guidewire capture sheath according to the first aspect of the invention to assume its first, contracted, condition;
(b) introducing the guidewire capture sheath according to (a) into the first vessel or a second vessel which communicates with the first vessel;
(c) advancing the guidewire capture sheath such that the capture means is directed towards the guidewire;
(d) causing or allowing the at least one portion of the capture means to assume its second, expanded, condition; and
(e) causing the guidewire and the capture means to approach one another, such that the guidewire is guided into the catheter by the capture means.

In a preferred embodiment the capture means is an eccentric cone which opens distally. "Eccentric" as used here means that the longitudinal axis of the catheter and the axis of the cone are not collinear. This relationship can be characterized in the terminology of conical structures. If a conical structure is defined as having a base and a vertex, then the perpendicular distance between the two is the height or altitude of the cone. A straight line from the vertex to a point of the base about which the base has rotational symmetry is the axis of the cone. Conical capture structures of this invention comprise what are more formally called "oblique" conical structures meaning that the vertex of the cone and the axis of the cone do not overlap and are not collinear. If the axis and the vertex of the cone coincide, then the cone is referred to as a right cone. If the base is circular (as opposed to elliptical or other shape) the cone is referred to as a right circular cone. For purposes of this invention, conical capture means or structures within its scope are all either "oblique" or "eccentric," those terms being used interchangeably herein.

BRIEF DESCRIPTION OF THE DRAWINGS

Thus, there is shown in FIG. 1 an embodiment of this invention that would be useful to capture the distal end of an antegrade-approaching guidewire 1 using a retrograde approaching catheter or capture device 10. Such a procedure might be employed e.g., to cross a lesion of the dorsalis pedis artery. Eccentric cone or funnel 12 is shown to be offset with respect to catheter tube 14, specifically offset with respect to its longitudinal axis. An eccentric funnel provides a wider capture area without inhibiting blood flow. Rotating the funnel moves the funnel mouth or opening 13 eccentrically within the artery.

FIG. 2 is a section view of the device of FIG. 1 taken along line 2-2 in FIG. 1. In FIG. 2, the view is generally antegrade, vessel 16, not being shown in FIG. 1. In FIG. 2 the eccentric cone 12 capture structure is clearly shown.

In FIG. 3, the eccentric cone capture structure 12 is shown having emerged from the lumen 20 of catheter 22. The device could ship in the open state. A collapsing tube with tapered tip could fold up the funnel and be used to feed it into the luer/backbleed device of the introducer or catheter.

FIG. 4 illustrates what is referred to herein as the cone's first i.e., collapsed condition. Upon exiting the catheter in the femoral site the funnel reopens. This provides a wide mouth goal for the approaching Pedal access guidewire.

Figure 4:
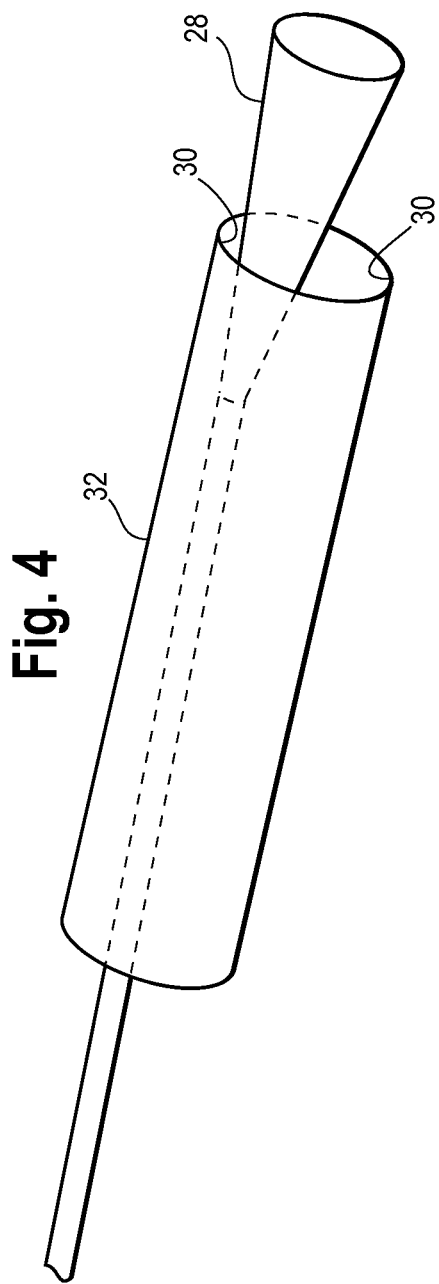
FIG. 4 shows a capture device 28 of this invention emerging from the lumen 30 of a further catheter configuration 32.
Figure 5:
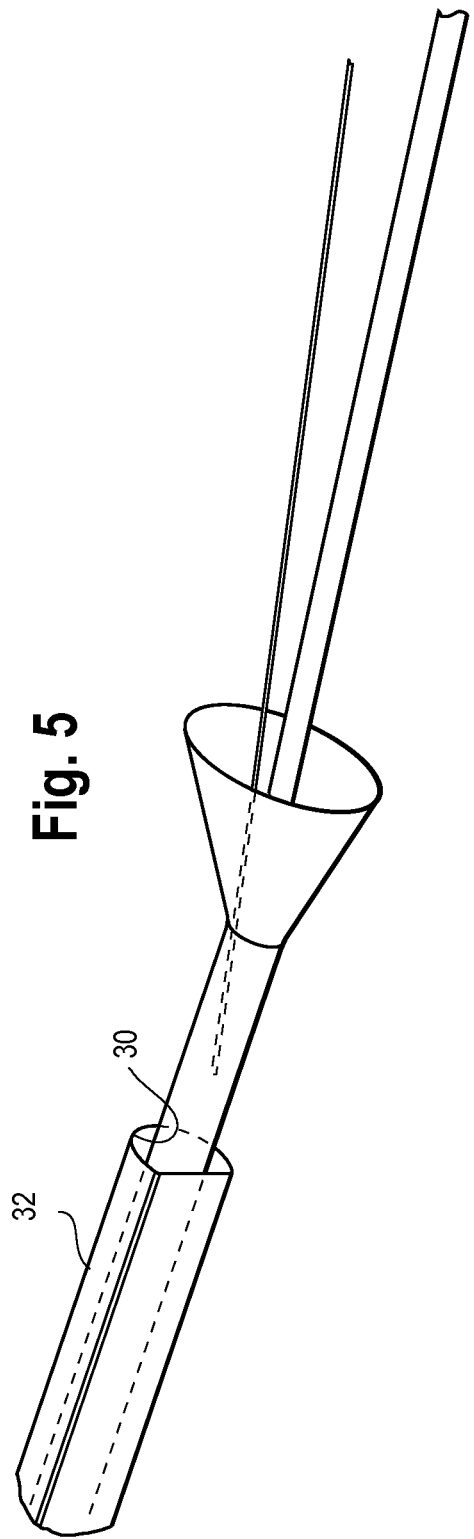
FIG. 5 shows the capture device of FIG. 4 in its second, i.e., expanding, (if not completely expanded) condition. A suitable material would recover into a smooth funnel.

In a further preferred embodiment, the capture means may be disposed within the catheter lumen when it is in the first, contracted, condition; and be caused to assume the second, expanded, condition upon being projected from the catheter, particularly a lumen defined by the catheter. Alternatively, the capture means may be permanently disposed to project from one end of the catheter. In one embodiment according to the latter case, the capture means is preferably configured so that when in a first, contracted, condition, it will form or define a substantially conical nose on the catheter that will assist the passage of the catheter through the bodily vessel by defining a flow-description-minimizing tip.

In some embodiments, it is preferable to introduce the guidewire capture sheath into the vessel with the guidance of a guidewire. In such embodiments, as the guidewire is inserted before the catheter of the guidewire capture sheath, it is preferable to provide an orifice within the capture means through which the guidewire may pass. Accordingly, when in its first, collapsed, condition, the capture means of these embodiments defines a guidewire-following aperture. As the catheter will be threaded over the distal end of this placement guidewire outside the body, it is only necessary that the guidewire following aperture be just sufficient to allow the catheter to be slid along the placement guidewire. Once the catheter has been placed in the vessel in which it is to capture a second guidewire, the capture means can be expanded to its second condition. In this second condition, it is preferable that the capture means expands to a size at which its outer parameter bears against only part of the circumferential luminal wall of the vessel. Partial circumferential overlap between the luminal wall and the outside of the capture means in the second condition, permits better luminal flow e.g., of blood, around the device while it is being used.

This is an important aspect of this invention and is one of the reasons the eccentric cone capture means of this invention is used. Having an non-central-axis-aligned cone deployed in a vessel provides laminar space between the outside perimeter of the cone to permit bodily fluids to flow by the capture means even during the guidewire capture process. The advantage of having bodily fluid flow around the outside of the cone is that downstream cellular and physiologic needs are at least partially met even during the guidewire capture process itself.

In preferred embodiments, such expansion provides assurance that as the guidewire and the guidewire capture sheath are caused to approach one another, the guidewire will eventually make contact with the capture means, and be funneled into the catheter. Typically, the guidewire will be projected down the catheter until its free end is located outside the body. The catheter can then be withdrawn from the vessel leaving the guidewire projecting from the vessel. A new catheter, such as a graft deploying catheter, can then be guided up the guidewire that has been captured by the guidewire capture sheath according to this invention.

There are a wide variety of forms that the capture means may take. In a first form, at least a portion of the capture means comprises a number of petal-like members disposed around the circumference of one end of the catheter. Each petal-like member is connected to its neighboring petal-like members by a web of a thin flexible film. In preferred embodiments, the petal-like members are pivotable between a first position, in which they are close together at their free ends, as are the petals in a flower bud, and a second position, in which they are spread apart, as in the manner of an opened flower. In the latter position, the petal-like members and the webs together form a funnel that will direct a guidewire into the lumen of the catheter. In this embodiment of the invention, the petal-like members may be caused to move between their first and second positions by a wire or wires connected to a radially outer side of one or more of the petal-like members, such that by pulling on the wire or wires the petal-like members are caused to be moved from their first position to their second position. Alternatively, the petal-like members may be formed as two superposed leaves connected at their free ends, an outer one of the leaves being connected at its base to the catheter and the inner end being connected at its base to a tube disposed within the catheter. In this arrangement relative movement between the catheter and the tube will move the petal-like members between their first and second positions. In a preferred form, a number of the petal-like members are at least semi-permeable to allow for additional passage of blood.

Also note that in embodiments of the invention where at least a portion of the capture means is comprised of a plurality of petal-like members, the materials and/or construction of at least that portion of the capture means may be such that no manipulative intervention is required to cause the petal-like members to go from their first position to their second position. An example of such embodiments includes cases where the capture means is formed of a material which has the capacity to "memorize" or "remember" a particular shape, and is, therefore, capable of memory-aided change. Such a material has a continuous tendency to return to that shape following any event which causes it to be temporarily deformed. A capture means with at least a portion being comprised of a plurality of petal-like members will, according to one such embodiment, be initially manufactured such that its petal-like members are pre-formed in their respective second-open-positions. Prior to introduction of the guidewire capture sheath into a vessel, such a capture means is then manually compressed and pushed into the lumen of the catheter, such that its petal-like members are caused to assume their respective first, closed, positions. Once the guidewire capture sheath is in the appropriate position within the vessel, the capture means is caused to extend beyond an end of the catheter e.g., by sliding engagement of one relative to the other. Such extension results in a release of the petal-like members from the confines of the catheter lumen, thereby allowing them to spring back into their respective second, open, positions. When the petal-like members are each in such a position, together, they preferably provide a funnel capable of directing a guidewire into the lumen of the catheter.

In further preferred embodiments, wherein at least a portion of the capture means is comprised of a plurality of petal-like members, the capture means is formed of a material which is capable of changing its shape when subjected to a change in temperature and is, therefore, capable of heat-aided change. In this case, the capture means will, upon introduction into a patient, undergo an increase in temperature caused by its placement within the body of the patient. It will, consequently, have its petal-like members change from their first, usually closed, position to their second, usually open, position. In such embodiments, it may be preferable, before using the invention, to predetermine the desired greatest cross-sectional diameter of the petal-like members when in their open, positions so that the radial size of this greatest cross-sectional diameter is appropriate to the circumstances of the particular case. In embodiments of the invention wherein temperature changes are employed to cause the capture means to assume the appropriate position for "capturing" a guidewire, materials such as Nitinol are preferably used in the manufacture of the capture means.

Naturally, in all of the embodiments so far described, wherein the capture means with petal-like members is formed of a "memory" material or a heat sensitive material, it may not be necessary to provide a means, such as a wire, which the surgeon must manipulate in order to cause the capture means to change from a first condition to a second condition. In these embodiments, such change may occur without manipulative intervention. Note that either metallic or non-metallic shape memory materials (or both) can be used.

In yet another embodiment of the invention, at least a portion of the capture means comprises a helical spring that is surrounded by an elastic sheath. In preferred arrangements of this embodiment, when in a relaxed state, the spring has a greater diameter at its free end than at an end which is connected to or integral with the catheter. In alternative arrangements of this embodiment, however, the spring may also have a constant diameter along its length when in the relaxed state. In either case, or for arrangements in which the diameter of the spring varies along its length, it is preferable that when in the relaxed state, the spring has, at least at one point, a diameter which is greater than the diameter of the catheter in which it is initially housed. Indeed, according to these embodiments, the spring is in the first condition housed within the catheter which holds it in a retracted condition. If a push rod extending long the catheter is used to push the free end of the spring out of the catheter (thereby allowing the spring to assume a relaxed state, the free end of the spring, and the elastic sheath attached to it, will then assume a second, expanded, condition. In this condition, the free end of the spring will engage against the luminal wall of a vessel in which the guidewire capture sheath has been deployed, and will direct a guidewire with which it comes into contact into the catheter.

As above, it is noteworthy that the discussion relating to the use of a "memory" materials, or those which respond to changes in temperature, for the formation of the capture means with a plurality of petal-like members is, in appropriate circumstances, equally applicable to the formation of a capture means which is essentially comprised of a spring.

In a still further embodiment, the capture means includes a distal portion of the first end of the catheter which, in at least its second condition forms a funnel member. The capture means of this embodiment is most preferably formed of either a shape "memory" material or a spring material. It may, however, also be formed of a material, such as Nitinol, which is capable of changing shape upon being subjected to a change in temperature or stress. In embodiments where the capture means is formed of the "memory" material, the catheter is housed within an outer sheath, and upon movement of the catheter relative the out sheath or e.g., a sliding movement, the capture means is caused to change from a first condition, in which it forms a part of the first end of the catheter, to a second condition, in which it forms the funnel member. In this second condition, the open end of the funnel member partially engages the luminal wall of a vessel in which the guidewire capture sheath has been deployed, and will direct a contra-directed guidewire into the catheter.

In similar embodiments, where the capture means if formed of a temperature sensitive material, such as Nitinol, there may, of course, be no need to provide an outer sheath as described above. This is because the capture means, according to this particular embodiment, will remain in its first, contracted, condition until such time as its temperature has increased to a point at which it changes to a second, expanded, condition.

While there are many operative procedures that could use the guidewire capture sheath according to the present invention, it is particularly useful in the procedures described in PCT patent specifications PCT/AU97/00046 and PCT/AU96/00714, the contents of both of which specifications are incorporated herein by reference.

In a further embodiment of the invention, the capture means comprises an eccentric helical spring that is surrounded by an elastic sheath. The spring has a greater diameter at its free end than at an end that is disposed within the first end of the catheter. The spring is in a first position housed within the catheter which holds it in a retracted condition. If a push tube, extending along the catheter, is used to push the free end of the spring out of the catheter, the free end of the eccentric spring, and the elastic sheath attached to it, will then assume a second condition and expand to its enlarged diameter. In this condition the free end of the eccentric spring will partially engage against the luminal wall of a vessel in which the guidewire capture sheath has been deployed and will direct a contra-directed guidewire into the catheter.

In a further embodiment the capture means includes a distal portion of the first end of the catheter formed form an eccentric shape memory material or eccentric spring material. The catheter is housed within an outer sheath, and upon deployment of the capture sheath within the appropriate vessel, the catheter is projected distal to the ends of the outer sheath by means of a push tube. Because the capture means is made from a shape memory material or spring material, upon projection beyond the distal end of the outer sheath, it will take on a second position in which it forms a funnel member. The open end of the funnel member abuts against the luminal wall of a vessel in which the capture sheath is being deployed. Accordingly, a guidewire being passed down the vessel will be guided into the lumen of the catheter by the funnel member of the capture device.

Incorporated by reference herein are the following patents and patent applications:

US 2005/0228402, "Methods and Devices for Percutaneous and Surgical Inventions," to Hofmann;

US 2007/0250070, "Medical Instrument Having a Medical Snare," to Nobis et al.;

WO 00/20064, "Guidewire Capture Device," to White et al.;

US 2008/0009883, "Snare Retrieval Device," to Bieneman;

US 2008/0221587, "Two-Stage Snare-Basket Medical Device," to Schwartz.

I claim:

1. A guidewire capture sheath for use in a bodily vessel, the guidewire capture sheath comprising:
   a) a catheter having a lumen extending along a longitudinal central axis from a proximal catheter open end to a distal catheter open end; and
   b) a capture cone that is connected to or integral with the catheter, wherein the capture cone comprises:
      i) a conical portion extending from a proximal conical open end to a distal conical open end, wherein the proximal conical open end is connected to or integral with the distal catheter open end; and
      ii) a cylindrical portion extending from a proximal cylindrical open end to a distal cylindrical open rim, wherein the proximal cylindrical open end is connected to or integral with the distal conical open end,
   c) wherein at least one portion of the capture cone is expandable from a first condition to a second condition having the conical portion being eccentrically oriented with respect to the longitudinal central axis of the catheter lumen, and wherein in the first condition, the cylindrical portion has a first cross-sectional area that is less than a second cross-sectional area of the conical portion in the eccentrically oriented second condition, the second condition thereby providing the distal conical open end and the cylindrical portion having greater respective diameters than the proximal conical open end so that the eccentrically oriented conical portion of the capture cone is configured to guide a guidewire into the cylindrical portion in open communication with both the conical portion and the catheter lumen.

2. The guidewire capture sheath according to claim 1, wherein when in the first condition, the at least one portion of the capture cone is contracted to a cross-sectional area that is relatively smaller than that of the catheter lumen, and when in the second condition, the at least one portion of the capture cone is expanded to a cross-sectional area that is relatively larger than that of the catheter lumen.

3. The guidewire capture sheath according to claim 1, wherein when in the first condition, the at least one portion of the capture cone is disposed within the catheter lumen, and when in the second condition, the at least one portion of the capture cone projects outwardly from the catheter lumen.

4. The guidewire capture sheath according to claim 1, wherein the capture cone is permanently disposed to project outwardly from the distal catheter open end.

5. The guidewire capture sheath according to claim 1, wherein the capture cone is comprised of Nitinol having a temperature sensitive memory.

6. A method for capturing a guidewire which is progressing along the lumen of a vessel, the method comprising:
 a) providing a guidewire capture sheath, comprising:
  i) a catheter having a lumen extending along a longitudinal central axis from a proximal catheter open end to a distal catheter open end; and
  ii) a capture cone that is connected to or integral with the catheter, wherein the capture cone comprises:
   A) a conical portion extending from a proximal conical open end to a distal conical open end, wherein the proximal conical open end is connected to or integral with the distal catheter open end; and
   B) a cylindrical portion extending from a proximal cylindrical open end to a distal cylindrical open rim, wherein the proximal cylindrical open end is connected to or integral with the distal conical open end,
  iii) wherein at least one portion of the capture cone is expandable from a first condition to a second condition having the capture cone being eccentrically oriented with respect to the longitudinal central axis of the catheter lumen and wherein in the first condition, the cylindrical portion has a first cross-sectional area that is less than a second cross-sectional area of the conical portion in the eccentrically oriented second condition, the second condition thereby providing the distal conical open end and the cylindrical portion having greater respective diameters than the proximal conical open end so that the eccentrically oriented conical portion of the capture cone is configured to guide a guidewire into the cylindrical portion in open communication with both the conical portion and the catheter lumen;
 b) introducing a guidewire into a first vessel;
 c) with the capture cone in its first condition, introducing the guidewire capture sheath into the first vessel or a second vessel in communication with the first vessel;
 d) advancing the guidewire capture sheath such so that the capture cone is directed towards the guidewire in the first or the second vessel;
 e) expanding the at least one portion of the capture cone from its first condition to its second, expanded condition; and
 f) causing the guidewire and the capture cone to approach one another so that the guidewire is guided into the cylindrical portion of the capture cone in open communication with both the conical portion and the catheter lumen.

7. The method according to claim 6 wherein the vessel is the dorsalis pedis artery and the guidewire crosses a lesion within the dorsalis pedis artery.

8. The method according to claim 7 including manipulating the guidewire to approach the guidewire capture sheath from an antegrade direction.

9. The method according to claim 6 further including rotating the guidewire capture sheath eccentrically within the vessel to help guide the guidewire into the cylindrical portion of the capture cone in open communication with both the conical portion and the catheter lumen.

10. The method according to claim 6 including providing the guidewire capture sheath comprising a material having a temperature sensitive memory.

11. The method according to claim 6, including expanding the at least one portion of the capture cone to its second condition once the guidewire capture sheath is in the desired location in the vessel.

12. The method according to claim 6, including sizing the capture cone so that with the capture cone in the second condition, an outer perimeter of the at least one portion of the capture cone partially bears against the luminal wall of the vessel in which the guidewire capture sheath is deployed.

13. The method according to claim 1, including deploying and retracting the capture cone into and out of the catheter lumen to thereby provide the capture cone in the respective second and first conditions.

14. A guidewire capture sheath for use in a bodily vessel, the guidewire capture sheath comprising:
 a) a catheter having a lumen extending along a longitudinal central axis from a proximal catheter open end to a distal catheter open end; and
 b) a capture cone that is connected to or integral with the catheter, wherein the capture cone comprises:
  i) a conical portion extending from a proximal conical open end to a distal conical open end, wherein the proximal conical open end is connected to or integral with the distal catheter open end; and
  ii) a cylindrical portion extending from a proximal cylindrical open end to a distal cylindrical open rim, wherein the proximal cylindrical open end is connected to or integral with the distal conical open end,
 c) wherein the capture cone is expandable from a first condition to a second condition having the conical portion being eccentrically oriented with respect to the longitudinal central axis of the catheter lumen, and wherein in the first condition, the cylindrical portion has a first cross-sectional area that is less than a second cross-sectional area of the conical portion in the eccentrically oriented second condition, the second condition thereby providing the distal conical open end and the cylindrical portion having greater respective diameters than the proximal conical open end so that the eccentrically oriented conical portion of the capture cone is configured to guide a guidewire into the cylindrical portion of the capture cone in open communication with both the conical portion and the catheter lumen.

15. The guidewire capture sheath according to claim 14, wherein when in the first condition, the distal conical open end is contracted to a cross-sectional area that is relatively smaller than that of the catheter lumen, and when in the second condition, the distal conical open end is expanded to a cross-sectional area that is relatively larger than that of the catheter lumen.

16. The guidewire capture sheath according to claim 14, wherein when in the first condition, the capture cone is disposed within the catheter lumen, and when in the second condition, the capture cone projects from the catheter lumen.

17. The guidewire capture sheath according to claim 14, wherein the capture cone is permanently disposed to project from the distal catheter open end.

18. The guidewire capture sheath according to claim 14, wherein the capture cone is comprised of Nitinol having a temperature sensitive memory.

\* \* \* \* \*

UNITED STATES PATENT AND TRADEMARK OFFICE
CERTIFICATE OF CORRECTION

PATENT NO. : 9,757,542 B2  Page 1 of 1
APPLICATION NO. : 13/895663
DATED : September 12, 2017
INVENTOR(S) : Henry W. Lupton It is certified that error appears in the above-identified patent and that said Letters Patent is hereby corrected as shown below:

In the Claims

Column 7, Line 54 (Claim 6, Line 40) delete the word "such"

Signed and Sealed this
Twenty-first Day of November, 2017

Joseph Matal
*Performing the Functions and Duties of the*
*Under Secretary of Commerce for Intellectual Property and*
*Director of the United States Patent and Trademark Office*